US012678036B2

(12) United States Patent
Giani et al.

(10) Patent No.: US 12,678,036 B2
(45) Date of Patent: Jul. 14, 2026

(54) INTRAORAL SCANNER, INTRAORAL SCANNING SYSTEM, METHOD FOR PERFORMING INTRAORAL SCANS AND COMPUTER PROGRAM PRODUCT

(71) Applicant: SOPRO SA, La Ciotat (FR)

(72) Inventors: Claudio Giani, Varese (IT); Giordano Pinarello, Turin (IT); Alessandro Bailini, Milan (IT); Francesca Nason, Milan (IT); Anna Cesaratto, Milan (IT)

(73) Assignee: SOPRO SA, La Ciotat (FR)

( * ) Notice: Subject to any disclaimer, the term of this patent is extended or adjusted under 35 U.S.C. 154(b) by 130 days.

(21) Appl. No.: 18/717,421

(22) PCT Filed: Dec. 7, 2022

(86) PCT No.: PCT/EP2022/084873
§ 371 (c)(1),
(2) Date: Jun. 7, 2024

(87) PCT Pub. No.: WO2023/104929
PCT Pub. Date: Jun. 15, 2023

(65) Prior Publication Data
US 2025/0040798 A1 Feb. 6, 2025

(30) Foreign Application Priority Data

Dec. 7, 2021 (EP) ..................................... 21212940

(51) Int. Cl.
*A61B 1/24* (2006.01)
*A61B 1/00* (2006.01)
(Continued)

(52) U.S. Cl.
CPC ............ *A61B 1/24* (2013.01); *A61B 1/00172* (2013.01); *A61C 9/006* (2013.01); *A61C 13/34* (2013.01)

(58) Field of Classification Search
USPC .......................................................... 348/66
See application file for complete search history.

(56) References Cited

U.S. PATENT DOCUMENTS 10,531,074 B2* 1/2020 Wilson ................. H04N 17/002
2005/0019722 A1* 1/2005 Schmid ..................... A61B 1/24
433/29

(Continued)

FOREIGN PATENT DOCUMENTS

CN 108175535 A 6/2018
WO 2019236934 A1 12/2019

OTHER PUBLICATIONS

International Search Report (Jun. 15, 2023) from PCTEP2022084873.
(Continued)

*Primary Examiner* — Nigar Chowdhury
(74) *Attorney, Agent, or Firm* — St. Onge Steward Johnston & Reens LLC; Stephen P. McNamara

(57) ABSTRACT

An intraoral scanner for intraoral stereovision comprises a projector for projecting a dot pattern onto an object to be imaged, the projector having a radiation source and optics for generating the dot pattern from radiation emitted by the radiation source, and at least two cameras for imaging the dot pattern projected on the object, the cameras being arranged for having an overlapping field of view on the object. The dot pattern is a non-periodic dot pattern generated by a two-dimensional array of microlenses arranged on a substrate in a non-periodic manner and the array of microlenses is the last beam shaping optical element before the object in the direction of the radiation.

16 Claims, 12 Drawing Sheets

(51) Int. Cl.
  _A61C 9/00_        (2006.01)
  _A61C 13/34_        (2006.01)

(56)            References Cited

U.S. PATENT DOCUMENTS

| | | | | |
|---|---|---|---|---|
| 2006/0227216 | A1 | 10/2006 | Mazuir | |
| 2013/0032914 | A1* | 2/2013 | Iwasaki | H10F 77/413 |
| | | | | 257/E31.127 |
| 2014/0043611 | A1* | 2/2014 | Narasimhan | G01J 1/0407 |
| | | | | 356/402 |
| 2016/0003610 | A1* | 1/2016 | Lampert | G02B 23/26 |
| | | | | 356/4.01 |
| 2017/0280986 | A1* | 10/2017 | Sekowski | H04N 23/56 |
| 2018/0213207 | A1* | 7/2018 | Wilson | A61B 1/0605 |
| 2018/0303314 | A1* | 10/2018 | Noyes | A61B 1/0669 |
| 2019/0379881 | A1* | 12/2019 | Tewes | G02B 3/0068 |
| 2019/0388194 | A1* | 12/2019 | Atiya | A61B 1/00193 |
| 2020/0169649 | A1* | 5/2020 | Ouyang | A61B 1/00064 |

OTHER PUBLICATIONS

Written Opinion of the International Searching Authority (Jun. 15, 2023) from PCTEP2022084873.

* cited by examiner

WD = 8 mm:

Stereo images

Disparity map

WD = 10 mm:

Stereo images

Disparity map

WD = 12 mm:

Stereo images

Disparity map

WD = 14 mm:

Stereo images

Disparity map

WD = 16 mm:

Stereo images

Disparity map

WD = 18 mm:

Stereo images

Disparity map

Functional blocks detail: Preprocessing

Functional blocks detail: core

Functional blocks detail: Model generation

Outliers removal ~81    ~80

Segmentation and cluster removal ~82

Duplicates removal ~83

Spatial filtering ~84

Mesh reconstruction ~85

Mesh cropping ~86

Color mapping ~87

Mesh smoothing ~88

Accuracy map $\mu = 14.4 \pm 2.1 \ \mu m$ $\sigma = 13.3 \pm 1.5 \ \mu m$

INTRAORAL SCANNER, INTRAORAL SCANNING SYSTEM, METHOD FOR PERFORMING INTRAORAL SCANS AND COMPUTER PROGRAM PRODUCT

FIELD OF THE INVENTION

The invention relates to the field of intraoral scanners for generating three-dimensional models of a dentition.

BACKGROUND OF THE INVENTION

WO 2019/236934 A1 discloses an intraoral scanner, that uses an array of microlenses for generating a pattern, that is imaged on the dentition by some further optics. The intraoral scanning system is arranged for generating a three-dimensional model of the dentition by triangulation.

A disadvantage of the known intraoral scanner is its complexity so that numerous components must be assembled for manufacturing the intraoral scanner.

SUMMARY OF THE INVENTION

The invention relates to an intraoral scanner comprising:
a projector for projecting a structured pattern onto an object to be imaged, the projector having a radiation source and optics for generating the structured pattern from the radiation emitted from the radiation source, and
at least two cameras for imaging the pattern projected on the object, the cameras being arranged for having an overlapping field of view on the object.

The invention further relates to an intraoral scanning system, a method for performing intraoral scans and a computer program product.

The present invention seeks to provide an intraoral scanner of reduced complexity and an associated intraoral scanning system, which is able to generate three-dimensional models of a dentition at least as precisely as conventional intraoral scanners. The invention further seeks to provide a corresponding method and a computer program product.

This object is achieved by an intraoral scanner, an intraoral scanning system, a method and a computer program product having the features described herein. Advantageous embodiments and refinements are specified as further described herein.

In the intraoral scanner, the pattern is a non-periodic dot pattern generated by a two-dimensional array of microlenses arranged on a substrate in a non-periodic manner and this array of microlenses is the last beam shaping optical element before the object in the direction of the radiation. Such an irregular array of microlenses is particularly useful for determining the surfaces of tissue in the oral cavity since the radiation emitted by the radiation source is completely used for generating the dot pattern. The dots of the pattern are consequently highly visible in the images taken by the cameras. Due to the high density of microlenses the dot pattern can also be very dense so that the structure of the dentition can be resolved with high accuracy. The microlens array also provides a high depth sharpness due to the small lateral extension of the microlenses. Thus, no further beam shaping optics is needed between the microlens array and the object, so that the complexity of the intraoral scanner is considerably reduced compared to conventional intraoral scanners.

It should be noted that, in the context of the present application, mirrors or planar windows shall not be considered as beam-shaping optical elements.

The rays of the beam arriving at the microlenses are generally not collimated so that no collimating optics is needed.

The microlenses are associated with subbeams within the beam and the subbeams converge on the object side of the array of microlenses.

As the rays of the beam arriving at the microlenses are generally not collimated, the working distance, at which the size of the dots is at a minimum, is consequently greater than the focal length of the microlenses, the working distance and the focal length each being measured in radiation direction from the base of the microlenses on the surface of the substrate.

The subbeams may be deflected in a lateral direction by at least one mirror positioned in front of and/or behind the array of microlenses in the direction of the radiation depending on the requirements to the size of the dot pattern on the object. If the mirror is positioned behind the array of microlenses the dot pattern may be bigger than the dot pattern that is obtained if the mirror is located in front of the array of microlenses, but in the latter case the intraoral scanner is more compact.

The mirror may also deflect incoming light towards the cameras, so that the field of view is expanded in correspondence with the expanded size of the dot pattern.

In one embodiment, the microlenses are arranged in a honeycomb structure, the center of each microlens being shifted off-center from the center of the corresponding honeycomb cell by a randomly selected distance and direction. This allows to maximize the density of microlenses whose boundaries are nearly circularly shaped.

The radiation source is generally a laser diode and the divergence of the beam emerging from the laser diode is homogenized by an optical element located between the laser diode and the array of microlenses.

The cameras are generally oriented in the same direction, since the cameras can easily be mounted side by side on the same circuit board. If the cameras are oriented in the same direction, the depth resolution is also maximized.

For allowing a sufficient overlap between the field of views of the cameras, the cameras are disposed next to each other and the center of the array of microlenses is located at a distance from the baseline between the cameras, usually below the cameras.

The array of microlenses may be tilted by an angle $\alpha$ towards an axis at right angle to a beam axis of the beam in order to equalize the distance between the microlenses and the surface of the object.

The angle $\alpha$ is generally more than half of an angle $\beta$ between the beam axis and an axis of a field of view of the cameras if viewed along a frontside of the substrate forming the base for the microlenses.

An intraoral scanning system for generating a three-dimensional model of a dentition using active stereo vision comprises an intraoral scanner as described above, wherein each camera generates a series of images patterns projected onto the dentition. The intraoral scanning system further comprises a data processing unit connected to the intraoral scanner for generating the three-dimensional model of the dentition based on disparity maps formed by means of a synchronized series of images generated by each camera.

The data processing unit of the intraoral scanning system is particularly arranged for performing the following acts:

capturing a series of synchronized images by means of the at least two cameras;

generating disparity maps based on pairs of synchronized images, wherein each image is taken from a different camera;

generating depth maps based on the disparity maps;

registration of the depth maps;

forming a mesh of points defining the surface of the imaged dentition.

A corresponding method for generating a three-dimensional model of a dentition based on active stereo vision, may comprise the following acts:

retrieving from the above described intraoral scanner a series of images of the dentition, using a data processing unit connected to the intraoral scanner for generating the three-dimensional model of the dentition based on disparity maps formed by means of the series of images generated by each camera of the intraoral scanner.

A computer program product contains program code for implementing the method when run on a data processing unit.

Further advantages and properties of the present invention are disclosed in the following description, in which exemplary embodiments of the present invention are explained in detail based on the drawings:

DETAILED DESCRIPTION OF THE INVENTION

Figure 1:
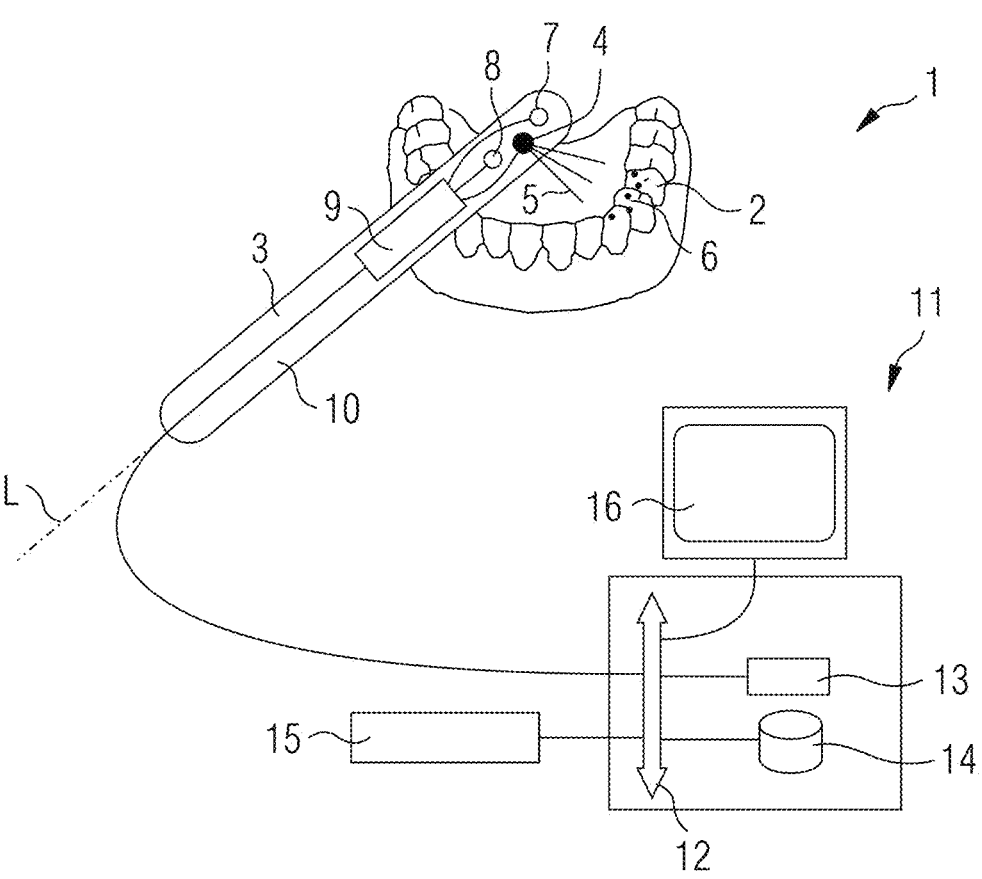
FIG. 1 is an intraoral scanning system.

FIG. 1 shows an intraoral scanning system 1 that can be used for generating a three-dimensional model of a dentition 2. The intra oral scanning system 1 comprises an intraoral scanner 3 extending along a longitudinal axis L. A projector 4 located within the scanner 3 emits radiation 5 and projects a dot pattern 6 onto the dentition 2. The dot pattern 6 is imaged by a first camera 7 and a second camera 8 in a synchronized manner. The operation of the projector 4, the first camera 7 and the second camera 8 may be controlled by a control unit 9 which may be located within a handle 10 of the scanner 3. The digital images generated by the first camera 7 and the second camera 8 are transferred to a data processing unit 11. The data processing unit 11 comprises a data bus 12, a processor 13 and storage means 14 for storing data such as the digital images and computer programs that might be used for processing the digital images as described herein. The data processing unit 11 may also be provided with the usual input means 15 such as a keyboard or a mouse and with the usual output means such as a display 16.

Figure 2:
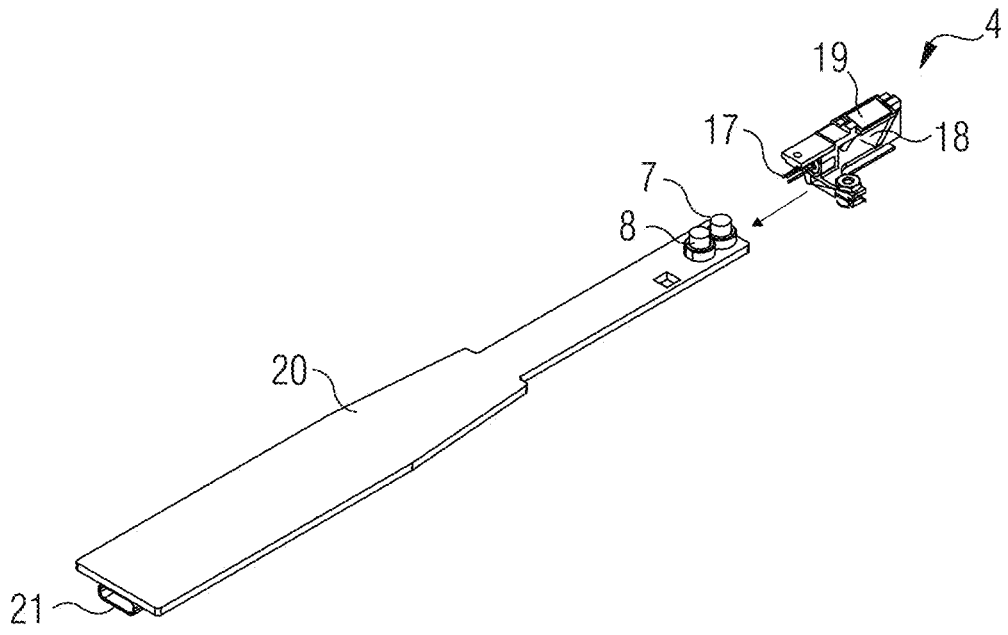
FIG. 2 is a perspective view of some internal components of the intraoral scanner from FIG. 1.

FIG. 2 is a perspective view of some inner components of the intraoral scanner 3. The projector 4 is disposed at the distal tip of the intraoral scanner 3. The projector 4 is provided with a radiation source formed by a laser diode 17 that emits the radiation 5 in a longitudinal direction towards the distal end of the intraoral scanner 3. The radiation 5 is deflected by a mirror 18 into a lateral direction. The deflected radiation impinges on a microlens array 19 that may also form the window, through which the radiation 5 for the dot pattern 6 leaves the intraoral scanner 3.

The laser diode 17 is typically operated in the power range of 20 to 100 mW and may emit radiation in the wavelength range between 400 to 500 nm. It has been found that a shorter wavelength results in a better spatial accuracy. The laser diode 17 may emit the radiation 5 at a wavelength in the range of 450 nm+/−5 nm or 405 nm+/−5 nm or preferably at a wavelength of about 450 nm or 405 nm. Taking into account the sensitivity of the cameras 7 and 8 it may be advantageous to use a wavelength of 450 nm+/−5 nm and in particular 450 nm, since the cameras 7 and 8 tend to be more sensitive at these wavelengths so that the ratio of signal-to-noise per spatial accuracy is maximized at this wavelength.

The projector 4 may further be provided with a secondary radiation source for illuminating the dentition 2 with additional radiation. This secondary radiation source is not shown in FIGS. 1 and 2. The secondary radiation source may be used for taking color pictures of the dentition 2 or for detecting tooth decay in particular for detecting caries as described in US 2006/0227216 AI, wherein the xenon lamp may be replaced by a LED emitting radiation within the ultraviolet to the near visible.

The intraoral scanner 3 further comprises a base plate 20, on which the first camera 7 and the second camera 8 are mounted. The base plate may also carry the control unit 9. The base plate 20 carries a connector 21 for connecting the intraoral scanner 3 to the data processing unit 11.

Figure 3:
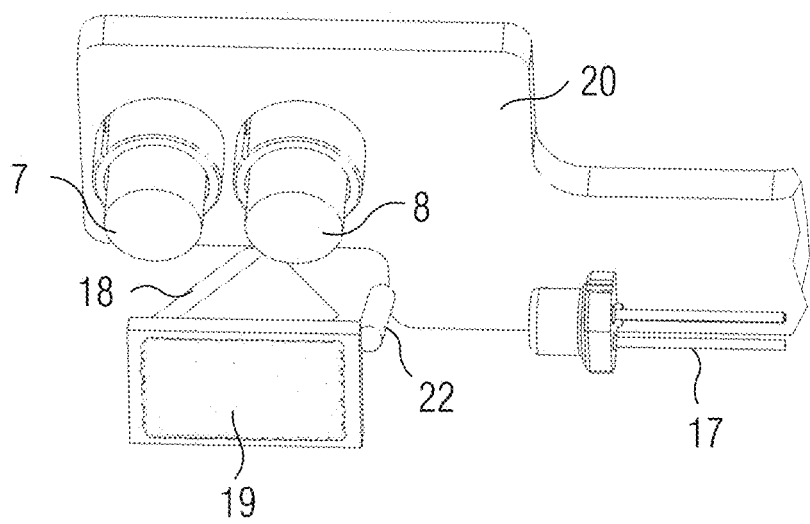
FIG. 3 is a perspective front view on a projector and cameras of the intraoral scanner.

FIG. 3 is a perspective front view of the projector 4 and the two cameras 7 and 8. The projector 4 includes the laser diode 17. The projector 4 is further provided with a rod lens 22 that is used as a beam shaping optics as will be explained later on. The mirror 18 and the final microlens array 19 follow the rod lens 22 along the path of the radiation 5.

Figure 4:
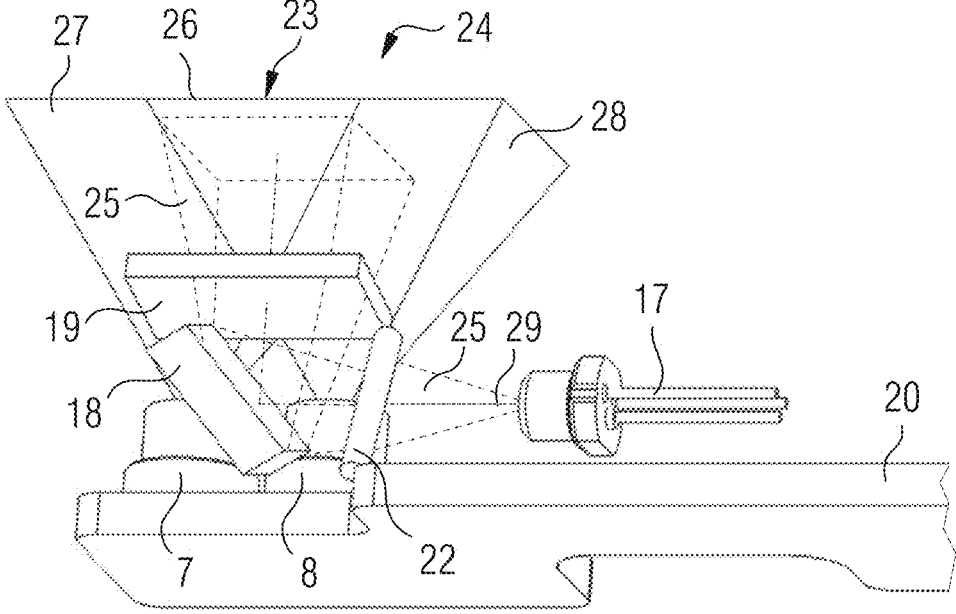
FIG. 4 is a perspective view of a beam path of a radiation beam emitted by a laser diode of the projector.

FIG. 4 illustrates the path of the radiation 5 from the laser diode 17 to a surface 23 of an object 24, on which the dot pattern 6 is to be projected. The radiation 5 emerges from the laser diode 17 as a radiation beam 25, which has an elliptical cross section. The rod lens 22 widens the beam divergence of the radiation beam 25 in one direction so that the beam divergence becomes more uniform in all directions. The radiation beam 25 transformed by the rod lens 22 impinges on the mirror 18, which deflects the radiation beam 25 in a lateral direction towards the microlens array 19.

The microlens array 19 is oriented parallel to the longitudinal axis L of the intraoral scanner 3. The dot pattern 6 is thus projected in a lateral direction with regard to the longitudinal axis L of the scanner 3 such that the dot pattern 6 is located within a scan area 26, which is defined by an overlapping region of a field of view 27 of the first camera 7 and a field of view of the second camera 8, whose field of views 27 and 28 are also oriented in a lateral direction so that the scan 26 covers at least part of the dot pattern 6.

Figure 5:
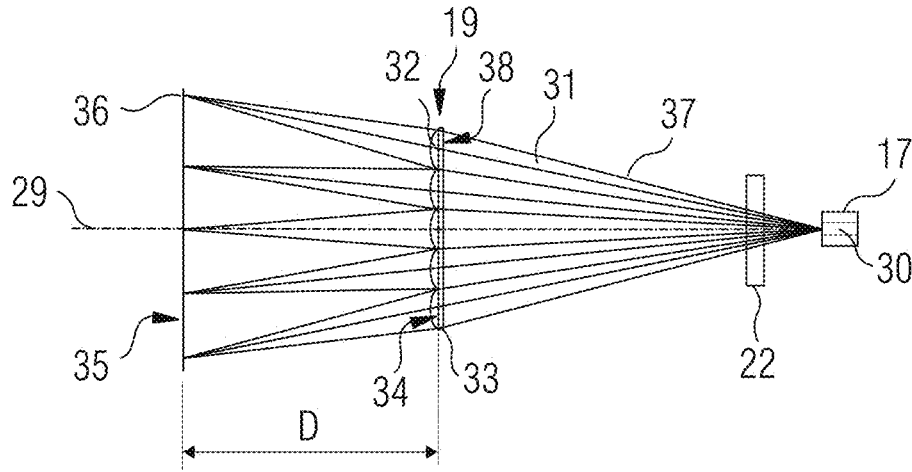
FIG. 5 shows the beam path of the rays impinging on a beam forming microlens array, wherein the beam path is shown in the plane of a radiation emitting region of the laser diode.

In FIG. 4, the radiation beam 25 is shown to follow a beam axis 29. FIG. 5 is a cross-section through the radiation beam 25 along the beam axis 29 in the plane of a radiation emitting region 30 of the laser diode 17. This light emitting region 30 may be the planar pn-junction of the laser diode 17.

For the sake of simplicity, the mirror 18 is omitted in FIG. 5.

As can be recognized from FIG. 5, the radiation beam 25 comprises a number of subbeams 31 formed by microlenses 32 of the microlens array 19. The microlenses 32 are arranged on a substrate 33 that is transparent for the radiation 5 emitted by the laser diode 17. The microlenses 32 are formed on a front side 34 of the substrate 33, wherein the front side 34 is the side facing the object 24. The microlenses 32 of the microlens array 19 are semi-convex lenses, whose flat bases are disposed on the front side 34 of the substrate 33 and whose curved side are facing the object 24. The radius of curvature is typically in the range of 2 to 3 mm, which corresponds to focal lengths of 4 to 6 mm. The radius of curvature may be for instance 2.5 mm, which corresponds to a focal length of 5 mm. The microlens array 19 may extend over a total area of 20 to 70 mm2. The density of the microlenses 32 may be in the range of 1200 to 6000 per cm2.

The microlenses 32 may be made from polymethylmethacrylate (PMMA) or from polycarbonate (PC), since both show suitable moldability. The radius of curvature depends on the required focal length and the type of material used for forming the microlenses 32. The radius of curvature in the range of 2 to 3 mm is also adapted to the material.

Each microlens 32 images the exit pupil of the laser diode 17 to a separate area on the surface 23 of the object 24, thus generating the dot pattern 6 on the surface 23 of the object 24. The projection of the dot pattern 6 focuses in a projection surface 35 which is defined by the places where each subbeam 31 converges to a dot 36, which means that the lateral extension of the cross section of the respective subbeam 31 is at a minimum. The projection surface 35 is generally a plane if all microlenses 32 have the same focal length.

Each dot 36 of the dot pattern 6 on the projection surface 35 is an image of the exit pupil of the laser diode 17. Since the rays impinging in each subbeam 31 on the microlenses 32 are not collimated but diverging, the focal length of the microlenses 32 is shorter than an object distance D, wherein the object distance D is the distance of the projection surface 37 from the front side 34 of the substrate 33 along the beam axis 29.

The only beam shaping optical element besides the microlenses 32 is the rod lens 22 that is disposed between the microlens array 19 and the laser diode 17. In the plane of the radiation emitting region 30, the rod lens 22 leaves the subbeams 31 unchanged. In the plane of the radiation emitting region 30 the rod lens 22 thus has only the effect of a planar window.

It should be noted that, in the context of the present application, mirrors or planar windows shall not be considered as beam-shaping optical elements. In a modified embodiment, the microlens array 19 may thus be protected by an exit window that is located between the microlens array 19 and is the object 24. In a further modified embodiment, the radiation beam 25 can be deflected into a lateral direction by a mirror that is disposed behind the microlens array 19 in the direction of the radiation 5. This mirror may be an additional mirror besides the mirror 18 or may replace the mirror 18.

Due to the small lateral extension of the microlenses 32, the orientation of edge rays 37 defining the subbeams 31 on the object side of the microlens array 19 converge at small angles. Thus, the cross section of the subbeams 31 vary slowly along the beam axis 29. The dot pattern 6 consequently comprises a large depth sharpness, which is advantageous given the fact that the intraoral scanner 3 is not always held at a defined distance from the dentition 2 so that the projection surface 35 generally fails to coincide with the surface 23 of the object 24. In addition, the surface 23 of the object 24 generally does not form a plane.

The microlens array 19 has further the advantage that the radiation 5 emitted by the laser diode 17 is completely used for generating the dot pattern 6, since no radiation absorbing stop mask is needed for generating the dot pattern 6.

Figure 6:
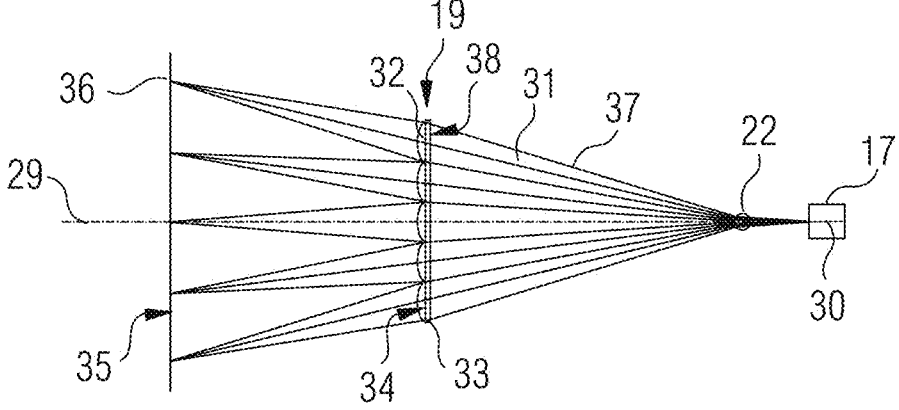
FIG. 6 shows the beam path of the rays impinging on a beam forming microlens array, wherein the beam path is shown in a plane at right angle to the plane of the radiation emitting region of the laser diode.

FIG. 6 shows the beam path of the subbeams 31 associated with individual microlenses 32 in a plane at right angle to the plane of the radiation emitting region. As in FIG. 5, the mirror 18 has been omitted for the sake of simplicity.

It can be recognized from FIG. 6 that the rod lens 30 increases the divergence of the radiation beam 25 emitted by the laser diode 17 such that the beam 25 illuminates the microlens array 19 completely.

As mentioned above, the beam 25 of the laser diode 17 has an elliptical cross-section, because the beam divergence in the plane of the radiation emitting region 30 of the laser diode 17 is greater than the beam divergence in a direction at right angle to the plane of the radiation emitting region 30. The rod lens 22 homogenizes the divergence of the beam 25 in that the rod lens 22 increases the beam divergence in the direction at right angle to the plane of the radiation emitting region 30. The longitudinal axis of the rod lens 22 is therefore located in the plane of the radiation emitting region 30 of the laser diode.

It should be noted that the microlenses 32 need not necessarily to be located on the front side 34 of the substrate 33. Instead, the microlenses 32 may also be disposed on the opposite rear side 38 of the substrate 33 facing the laser diode 17. In this case the focal length of the microlenses 32 should be shorter than the distance between the surface of the substrate 33 and the exit pupil of the laser diode 17 that is imaged to the projection surface 35.

Figure 7:
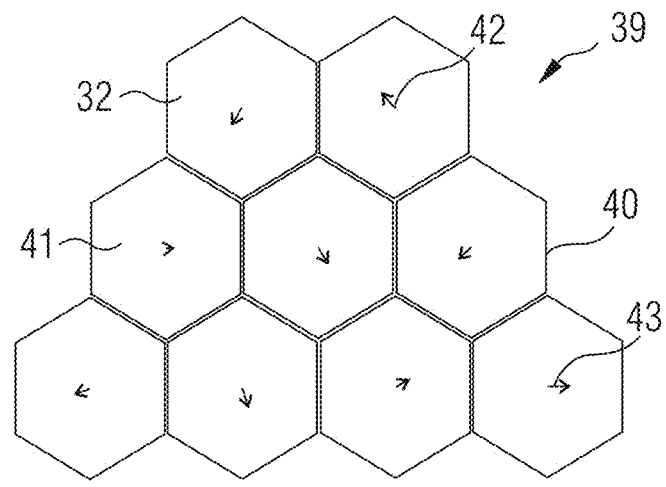
FIG. 7 illustrates the outline and spatial arrangement of the beam forming microlenses.

FIG. 7 is a view from above on the microlens array 19. The microlenses 32 are arranged on a hexagonal grid that forms a honeycomb structure 39, in which hexagonal honeycomb boundaries 40 define honeycomb cells 41.

For allowing a sub pattern of the projected pattern to be identified within the dot pattern 6, the microlenses 32 are arranged in a non-periodic manner. The center of each microlens 32 is linearly shifted by a randomly selected amount in a randomly selected direction, wherein the amount of the shift is smaller than the distance of the honeycomb boundary 40 from a honeycomb center 42 in the selected direction. The amount of the shift is typically in the range of 10 to 20% of the distance from the honeycomb center 42 to the honeycomb boundary 40. The direction and the amount of the shift is indicated in an exemplary manner by displacement arrows 43. Thus, the position of a subpattern of the dot pattern 6 can be identified in a digital image by calculating a correlation function of the digital image data with the searched subpattern of the dot pattern 6. After the position of the searched subpattern has been identified, even the position of individual dots 36 can be determined.

The dimensions of the microlenses 32, in particular their thickness and their radius of curvature, is chosen such that the microlenses 32 abut upon each other leaving no gap between the microlenses 32. Within the honeycomb structure 39, the outlines of the microlenses 32 at the outer surface of the microlens array 19 are thus generally at a distance from the front side 34 of the substrate 33.

The advantage of arranging of the microlenses 32 in the honeycomb structure 39 is that the honeycomb boundaries 40 of the microlenses 32 are nearly circular. In comparison to a microlens array having the microlenses arranged on a rectangular grid, lens errors that are most effective at large distance from the microlens center, in particular near the corners of the outline are diminished. The honeycomb structure 39 further allows to maximize the density of dots 36 in the dot pattern 6.

Figure 8:
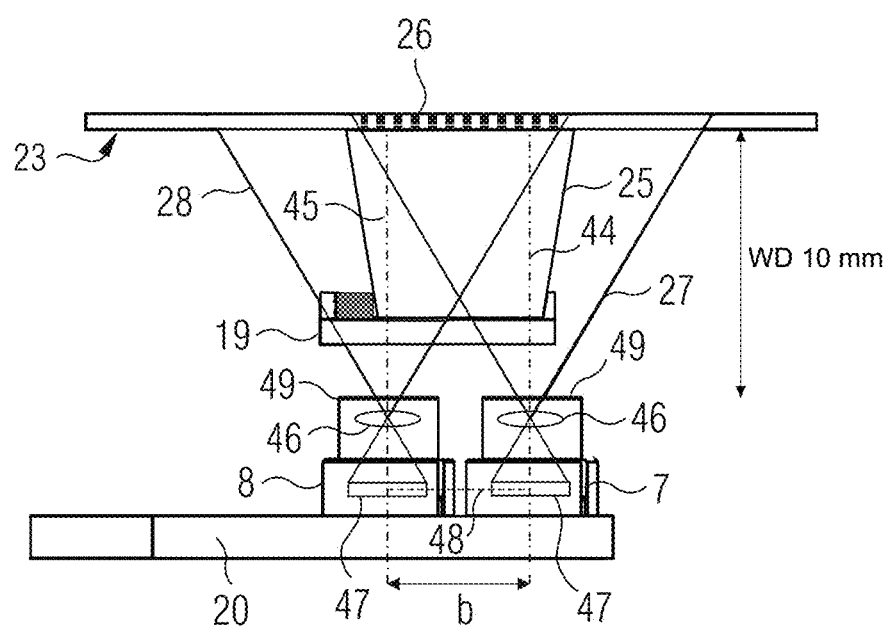
FIG. 8 is a view from above on the camera system of the intraoral scanner.

FIG. 8 is a view from above on the cameras 7 and 8 and their respective fields of view 27 and 28. The cameras 7 and 8 may both be mounted on the base plate 20 such that respective axes 44 and 45 of the fields of view 27 and 28 are oriented in the same direction. Both cameras 7 and 8 are provided with a camera optics 46 which images the object 24 including the dot pattern 6 on a sensor 47, which is generally a sensor chip generating a digital image of the object 24 and the dot pattern 6.

The fields of view 27 and 28 of both cameras 7 and 8 have a rectangular shape with the longer side of both fields of view 27 and 28 extending along a baseline 48 of length b that extends between the centers of the sensors 47 in the two cameras 7 and 8. The length b of the baseline 48 is selected such, that the fields of view 27 and 28 of both cameras 7 and 8 overlap. The overlapping region of both fields of view 2 and 42 is the scan area 26, which typically shows a width comprised between 9 and 20 mm and a height comprised between 7.5 and 16 mm.

The cameras 7 and 8 may further be provided with wavelength filters 49 disposed in the optical path of the radiation coming from the object 24 and impinging on the sensor 47. The wavelength filter 49 may for instance be disposed in front of the camera optics 46. Such a wavelength filter may be useful for detecting tooth decay or caries as described in detail in US 2006/0227216 A1.

It should be noted that the intraoral scanner 3 can be operated in two separate operation modes. In a first operation mode, in which the above-mentioned secondary radiation source is switched on and in which the laser diode 17 is switched off, color images of the dentition 2 may be taken. This operation mode may also be used for detecting tooth decay or caries in the dentition 2. In the second operation mode the laser diode 17 is used for generating three-dimensional models of the dentition 2.

The following explanations relate to the second operation mode for the generation of three-dimensional models.

Figure 9:
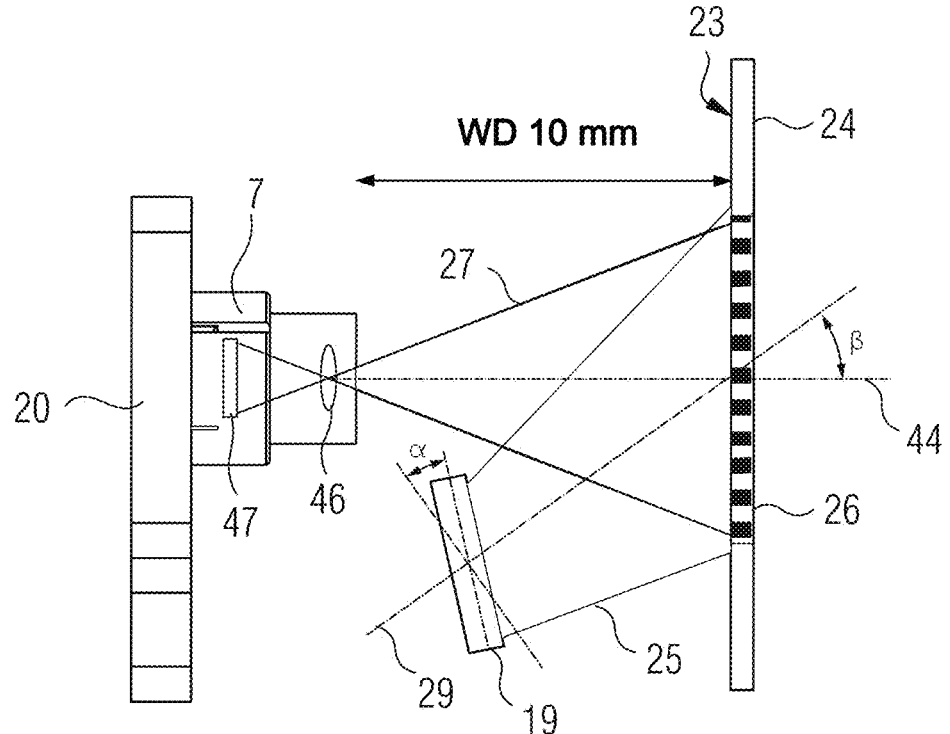
FIG. 9 is a side view on the projector and the camera systems of the intraoral scanner.

The microlens array 19 is located between the two cameras 7 and 8 below the two cameras 7 and 8 as depicted in FIG. 9 that shows a side view of the cameras 7 and 8 and the microlens array 19 of the projector 4. The microlens array 19 is arranged such that the projected dot pattern 6 falls at least partially within the scan area 26 of the cameras 7 and 8 for a large range of working distances WD. The working distance WD is the distance between the entry pupil of one of the cameras 7 and 8 and the scan area 26 measured along the axis 44 or 45 of the fields of view 27 or 28 of the camera 7 or 8. The microlens array 19 is tilted by an angle α in the range of 20° to 30° towards an axis at right angle to the beam axis 29 of the beam 25 in order to equalize the distance between the microlenses 32 and the surface 23 of the object 24. The angle α is generally more than half the angle β between the beam axis 29 and one of the axes of the field of view 44 and 45 if viewed along the frontside 34 of the substrate 33 that forms a base for the microlenses 32.

Figure 10:
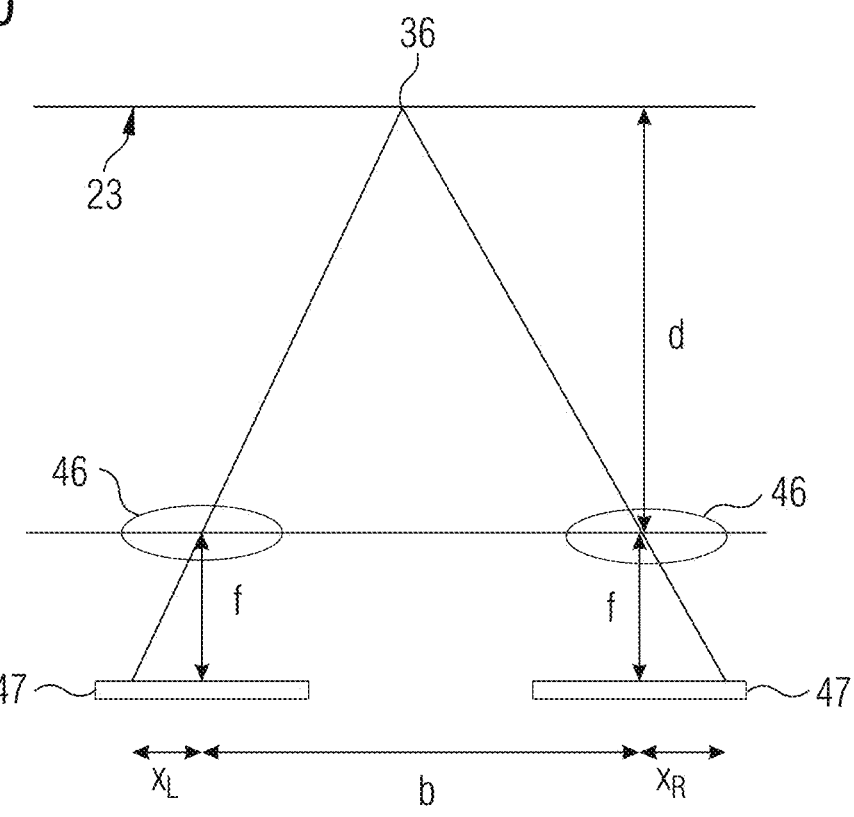
FIG. 10 illustrates the basic principle of stereo vision.

FIG. 10 illustrates the basic principle of computer stereovision. A point on the surface 23 of the object 24 is imaged on the sensor 47 of the first camera 7 at location $x_1$ and on the sensor 47 of the second camera 8 at location $x_2$. These images points are sometimes referred to as homologous points in both digital images. The centers of both sensor 47 are separated by the baseline b. The centers of the entrance pupils formed by the camera optics 46 are also separated by a distance having the length b. If the distance between the entrance pupil and sensor surface equals f, the distance d between the location of the dot 36 and the entrance pupil can be calculated based on the principles of central projection as:

$$d = \frac{b \cdot f}{x_1 + x_2}$$

The sum $x_1 + x_2$ is the so-called disparity. The disparity is thus inversely proportional to the distance d of the dot 36. Within the scan area 26 a so-called disparity map can be generated which show the disparity of each image point within the scan area 26. Graphic representations of disparity maps are usually encoded in a gray scale, wherein the gray level is inversely proportional to the disparity. That means that a point on the surface 23 of the object 24 at a smaller working distance WD appears to be brighter that a point on the surface 23 of the object 24 at a greater working distance WD.

Figure 11:
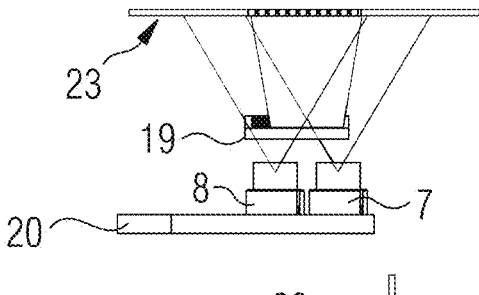
FIG. 11 illustrates the stereo vision at a working distance of 8 mm.
Figure 11:
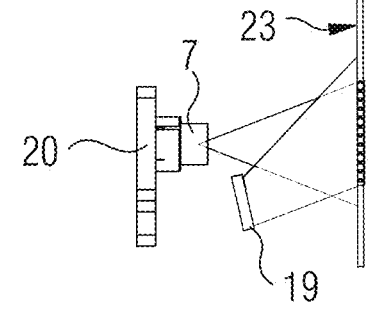
Figure 11:
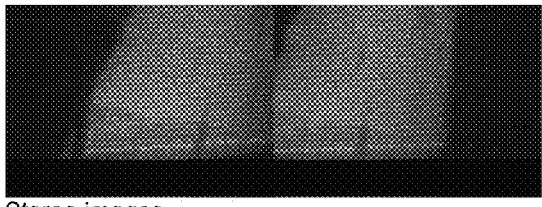
Figure 11:
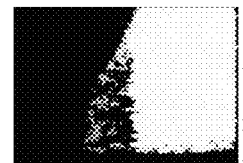
Figure 12:
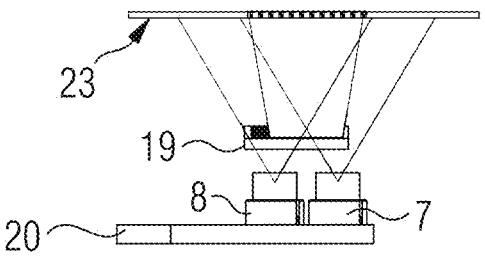
FIG. 12 illustrates the stereo vision at a working distance of 10 mm.
Figure 12:
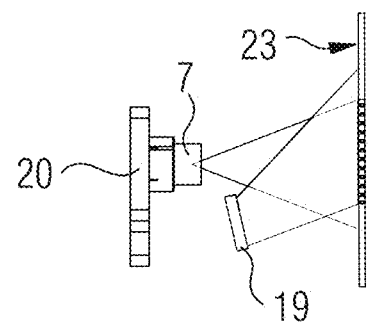
Figure 12:
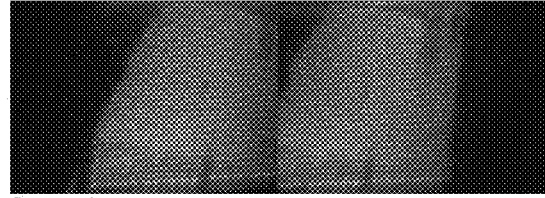
Figure 12:
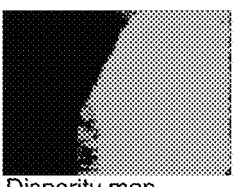
Figure 13:
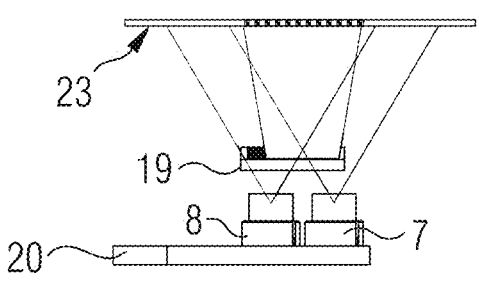
FIG. 13 illustrates the stereo vision at a working distance of 12 mm.
Figure 13:
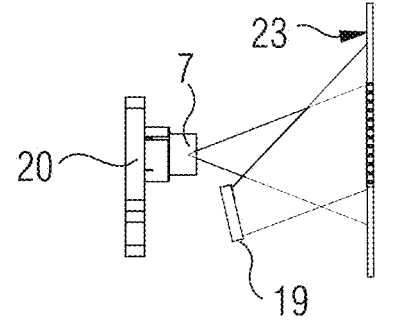
Figure 13:
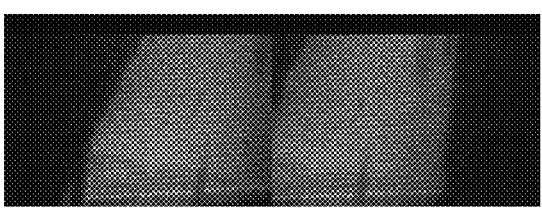
Figure 13:
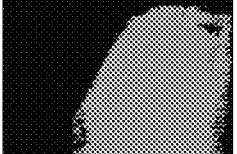
Figure 14:
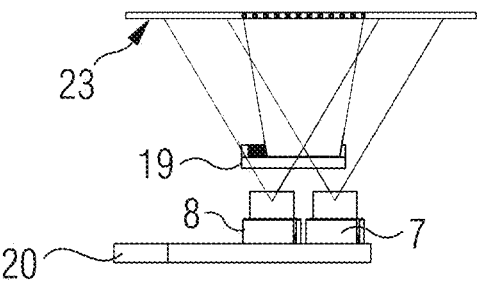
FIG. 14 illustrates the stereo vision at a working distance of 14 mm.
Figure 14:
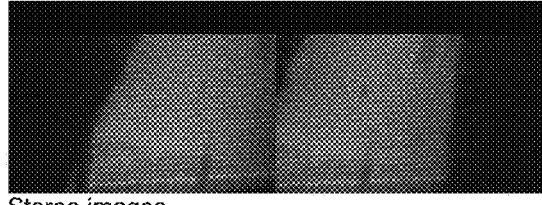
Figure 14:
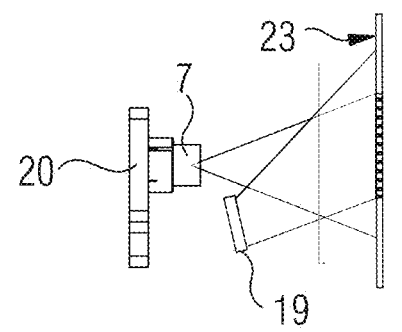
Figure 14:
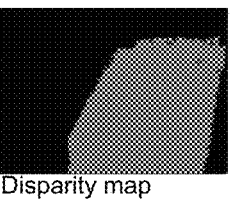
Figure 15:
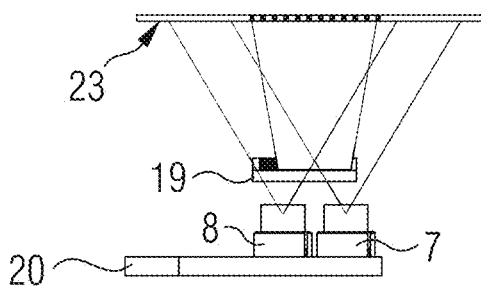
FIG. 15 illustrates the stereo vision at a working distance of 16 mm.
Figure 15:
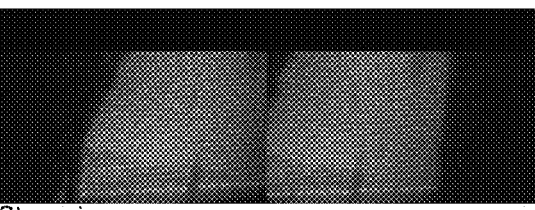
Figure 15:
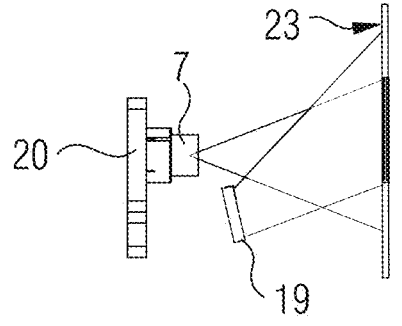
Figure 15:
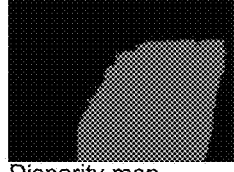
Figure 16:
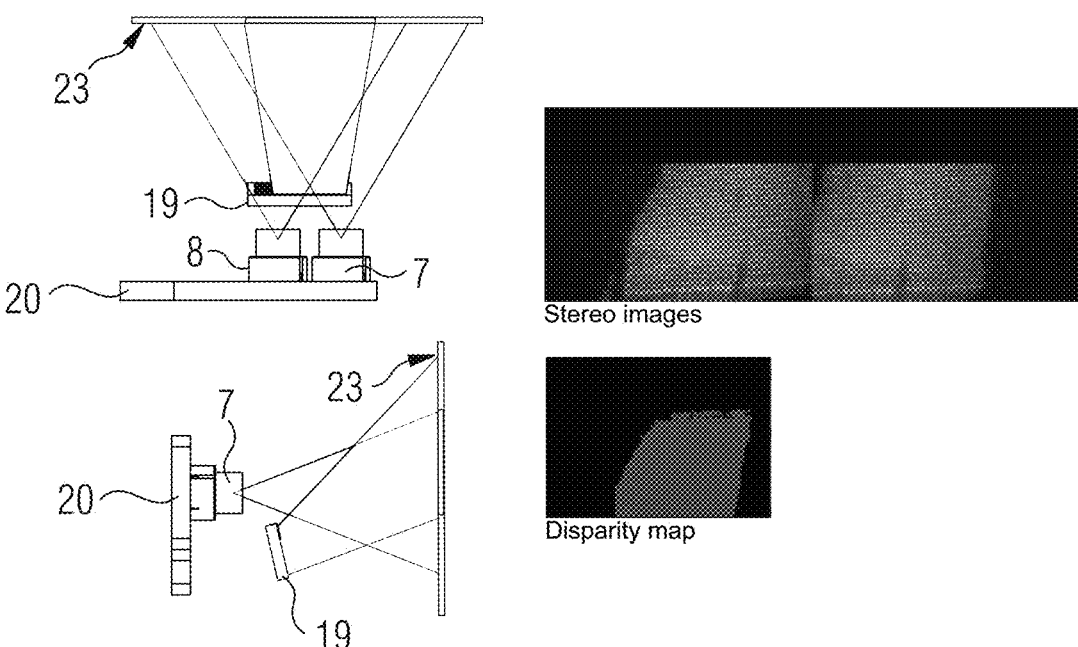
FIG. 16 illustrates the stereo vision at a working distance of 18 mm.

FIG. 11 show the spatial relations between projector 4 and cameras 7 and 8 at a working distance of 8 mm. The upper diagrams contain the left digital image of the dot pattern 6 taken by the first camera 7 and the right digital image taken by the second camera 8.

The lower diagram shows the resulting disparity map that is calculated based on the scan area 26 in which the digital left image and the digital right image overlap.

The subsequent FIGS. 12 to 16 correspond to FIG. 11 but with the working distances of 10 mm, 12 mm, 14 mm, 16 mm and 18 mm. In the disparity maps the disparity becomes increasingly darker indicating smaller disparity values corresponding to the increase of the working distance. At larger working distance the disparity is diminishing but still sufficiently great for determining the distance with sufficient accuracy.

The digital images taken by the two cameras 7 and 8 are processed according to the principle of active stereo vision (ASV), which, as such, is a method well-known in the art. In this method, structured light is projected onto the object 24 and the three-dimensional object 24 is reconstructed by determining the disparity in the overlapping scan area 26 based on pairs of digital images which are taken by at least one pair of cameras that are located at different locations.

Figure 17:
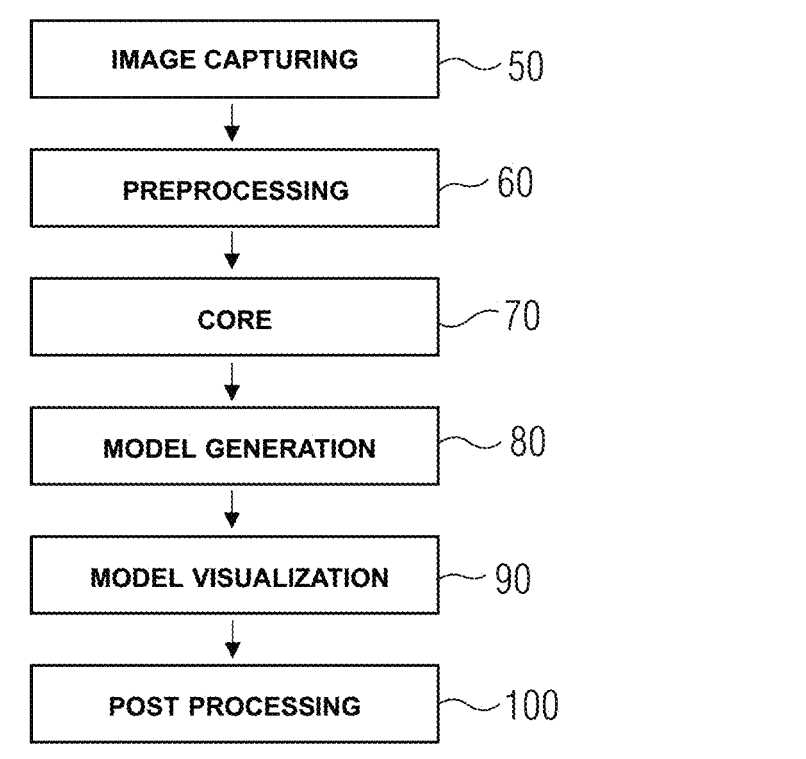
FIG. 17 shows a flow diagram of the data processing performed by data processing unit of the intraoral scanner.

FIG. 17 illustrates the principal steps of the method for reconstructing a three-dimensional image based on the digital images taken by the first camera 7 and second camera 8. The method may be performed by the processor 13 of the data processing unit 11 based on the digital images recorded by the cameras 7 and 8. In the following these digital images are also referred to as frames.

The method starts with an image capturing 50, a method step in which a series of digital images in true color with high density image quality generated by the cameras 7 and 8. The digital images or frames are taken by the first camera 7 and the second camera in a synchronized manner. The frame rate is typically in the range of 50 to 80 frames/sec.

In a subsequent preprocessing step 60, the frames are preprocessed. For instance, the imaged tissue may be automatically classified. Image regions relating to soft tissue are removed from the frames and margins between various objects are automatically detected. These tasks may be performed by a neural network or other forms of artificial intelligence.

In a method core 70, the information on the three-dimensional structure of the scanned dentition 2 is extracted from the image. For instance, depth maps are generated based on the disparity maps, the individual depth maps relating to different positions of the intraoral scanner 3 are combined and a mesh defining the surface of the dentition 2 is formed.

In a further model generation step 80, the three-dimensional model of the dentition 2 is formed.

In a visualization step 90, the constructed three-dimensional model can finally be visualized on the display 16 of the data processing unit 11.

In an optional post processing step 100, the three-dimensional model may be edited by the operator and finalized.

Figure 18:
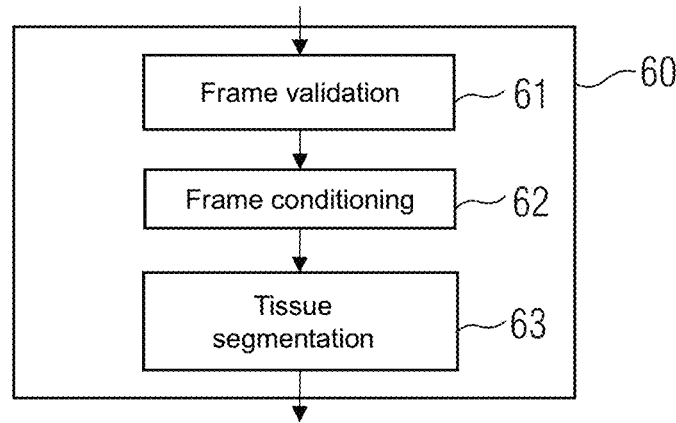
FIG. 18 illustrates details of a preprocessing.

FIG. 18 shows further detail of the preprocessing 60.

The preprocessing starts with a frame validation 61. In this step, the frames are analyzed to verify if they have the expected information content in order to make sure that the frames show an oral cavity.

The frame validation 61 is followed by a frame conditioning 62. In this step, the frames are prepared for the next processing step. The frames are rescaled, cropped, flipped and deskewed or equalized.

After the frame conditioning 62, the type of tissues imaged in the frames are segmented in a segmentation step 63.

Figure 19:
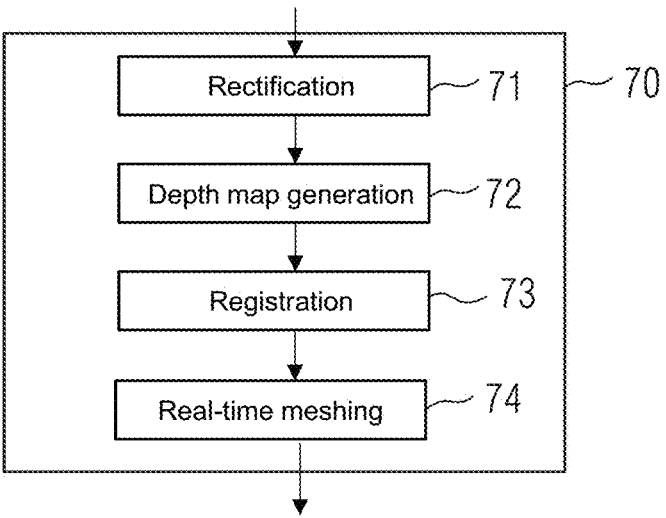
FIG. 19 shows details of the core data processing.

FIG. 19 further illustrates the core of the method.

As a first step a rectification 71 is performed. The rectification 71 applies to corresponding frames generated by the first camera 7 and the second camera 8 at the same point of time. Both frames are remapped so that homologous points in the two frames lay on horizontal lines. In a subsequent depth map generation 72, the homologous points in the two frames are matched and the disparity between them is stored in a disparity map. From the disparity map, a depth map of the scene is obtained according to the principles of stereovision as set forth above in connection of FIG. 10.

With each new pair of frames, the newly generated depth map is added to the previous ones by registration 73 using a registration algorithm, based on matching of homologous three-dimensional points of the depth maps to form a global point cloud.

The resulting point cloud is subjected to a progressive meshing 74. The progressive meshing 74 allows to visualize the incrementally growing three-dimensional scene in real time on the display 16.

Figure 20:
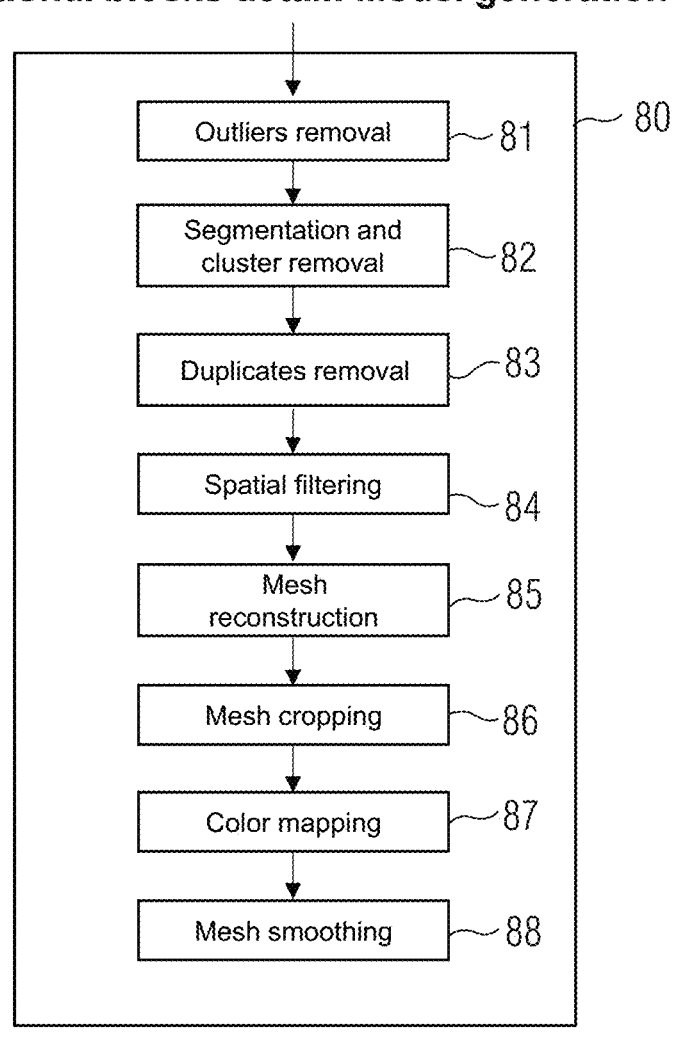
FIG. 20 depicts details of the model generation performed during data processing.

FIG. 20 shows further details of the subsequent model generation 80.

In a removal of outliers 81, isolated and irrelevant points not belonging to the surface of the scene are removed from the point cloud to reduce noise over the final mesh.

By a segmentation and cluster removal 82, group of points which represent cluster not belonging to the surface 32 are recognized and removed from the point cloud to avoid protrusions of the final mesh.

The number of points in the point cloud is subsequently reduced. In a removal of duplicates 82, vertexes in the point cloud, which are at zero Euclidean distance are merged.

As needed, further filters are applied. A spatial filter 84 may be applied, which maintains the same topology as the original point cloud, but includes only a fraction of the original points.

The filtered and decimated point cloud is then used in a 3D mesh reconstruction 85 to obtain a so-called watertight mesh surface based on the points positions and surface normals.

A mesh cropping 86 is then performed on the watertight mesh surface to limit its extension of the original point cloud as well as to remove eventual isolated polygons.

By color mapping 87 the color information contained in color images of the scene may reassigned to the mesh surface all over the mesh.

Mesh smoothing 88 may finally be used to regularize the surface and reduce polygon noise.

Figure 21:
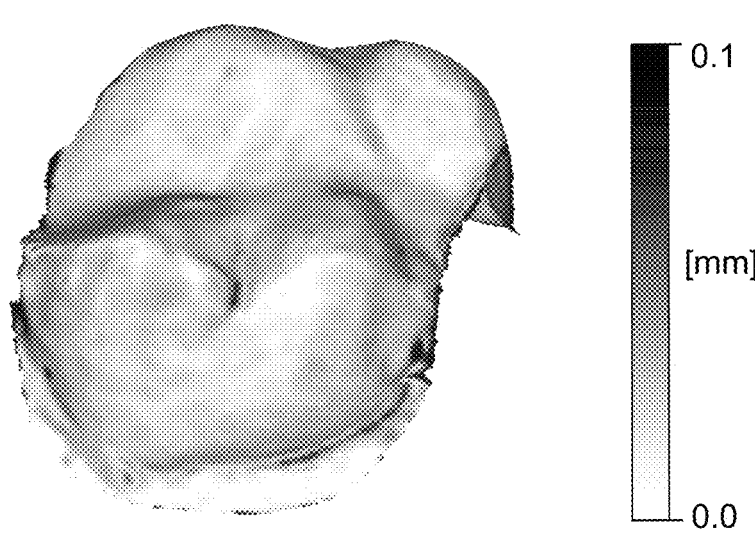
FIG. 21 demonstrates the surface resolution obtained by the intraoral scanner, FIG. 22 a perspective view of the tip region of a modified embodiment.

FIG. 21 illustrates the results of a test performed with the intraoral scanning system described herein. The intraoral scanning system was tested by scanning a tooth surface at a working distance of 10 mm using a microlens array 19 having a total of 1800 microlenses 32.

The grey shading indicates the accuracy of the reconstructed three-dimensional model. The mean accuracy is in the range of 14 μm. The accuracy over the whole three-dimensional model varied according to a distribution having a variance σ in the range of 13 μm.

The system and the method described herein are based on the principle of active stereo vision (ASV). It should, however, be noted that the images can also be evaluated based on the principle of structured-light stereo (SLS). In this method, the differences in pairs of images are evaluated as described herein according to the principles of active stereo vision. Additionally, the images of each camera are evaluated for deviations from a reference images at a reference distance. From these differences a depth map can be calculated. In the art, this additional evaluation is also referred to as triangulation. One problem with triangulation, however, is the calibration of the reference images. Therefore, considerable effort is needed for retrieving the additional depth information by triangulation.

Figure 22:
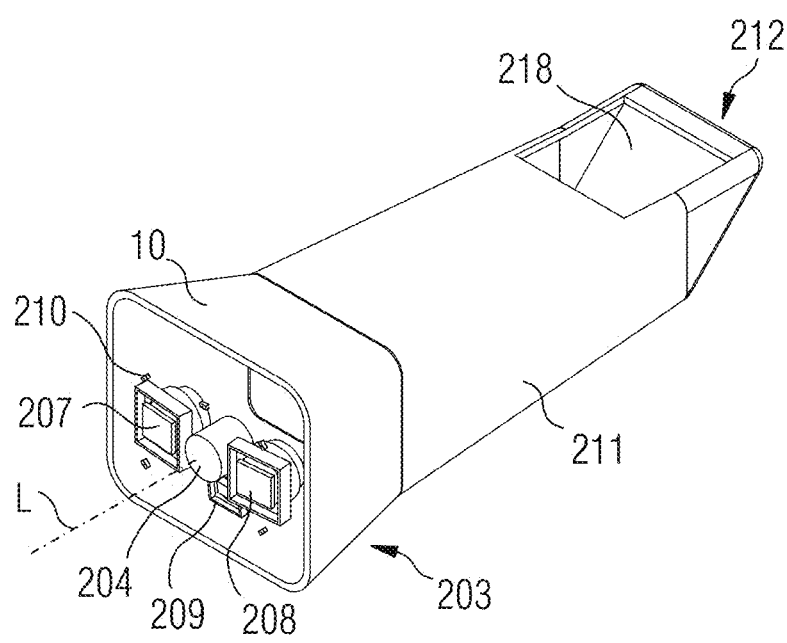

FIG. 22 shows a portion of a modified embodiment of the intraoral scanner 3. FIG. 22 particularly shows a distal end portion 203 of the handle 10, which is provided with a modified projector 204, which comprise the same components as the projector 4 except that the mirror 18 is omitted. The projector 204 thus projects the dot pattern 6 along the longitudinal axis L. The distal end portion 203 is further provided with a first camera 207, a second camera 208, and a third camera 209 that are disposed around the projector 204 and are either capable to take color and/or gray-scale images. The distal end portion 203 may further be provided with LEDs 210 for illuminating the dentition 2, for example with UV-light. The projector 204, the first camera 207, the second camera 208 and the third camera 209 can be used for active stereovision as described above as well as well as for passive stereovision or triangulation. The distal end portion 203 may also be provided with a hollow tip 211. At a distal end 212 of the tip 211, a mirror 218 is provided that deflects the beam 25 in a lateral direction. The tip 211 may be detachable from the handle 10. The tip is further autoclavable and may be provided with a heating element and/or a suitable coating for inhibiting fogging of the mirror 218.

The tip 211 allows to expand the size the dot pattern 6 since the optical path is longer and the lateral expansion of the dot pattern 6 at right angle to the beam axis 29 is larger than in the embodiment of FIGS. 1 to 16. The focal lengths of the microlenses 32 used for the projector 204 must correspondingly be longer and the radius of curvature of the microlenses 32 bigger than in the embodiment shown in FIGS. 1 to 16. The embodiment of FIG. 22 allows optical path length and working distance WD up to 50 mm.

Figure 23:
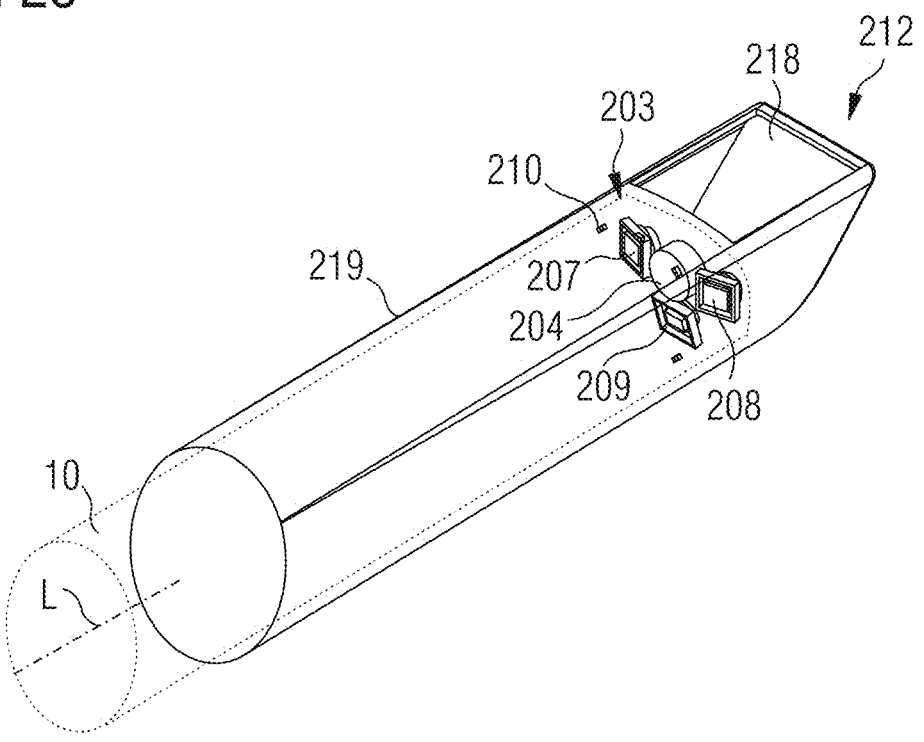
FIG. 23 a perspective view of the tip region of a further modified embodiment.

FIG. 23 shows a further modified embodiment of the intraoral scanner 3. FIG. 23 depicts again the distal end portion 203 of the handle 10. The distal end portion 203 is covered by the sleeve-shaped tip 219 that can be removed from the distal end portion 203 of the handle 10. In comparison with the embodiment shown in FIG. 22, the embodiment of FIG. 23 allows a shorter optical path and working distance WD above 20 mm.

For generating the color images of the dentition 2, the laser diode 17 and the secondary radiation source may be activated alternatively and corresponding images may be taken by the cameras 7 and 8. The images taken under illumination by the secondary radiation source may then be used for the color mapping 87 for generating a three-dimensional model with colored surfaces of the dentition 2.

The data processing unit 11 can be a computer having at least one physical or logical processor 13. The data processing unit 11 can also be implemented on several physical computers or can be an integrated device including the display 16.

It should also be noted that the method can be implemented by a computer program product, that contains code for implementing the method described herein, if the code is executed by a processor either in the data processing unit 11 or in some other entity. In some embodiments, the computer program product may be code stored on a computer readable data carrier such as a disc, a compact disc or a digital versatile disc or the like. In other embodiments, the computer program product may also be code stored on a data storage unit on a server or an array of servers. Such a data storage unit may be a hard disc or an array of hard disc or the like. In further embodiments, the data carrier may also be an electrical carrier signal that can be used for transferring the code from a server, which can be used for downloading the program code to a client.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds or groups described in conjunction with a particular aspect, embodiment or example of the invention are to be understood to be applicable to any other aspect, embodiment or example described herein unless incompatible therewith.

The invention claimed is:

1. An intraoral scanner comprising:
   a projector for projecting a structured pattern onto an object to be imaged, the projector having a radiation source emitting a beam and optics for generating the structured pattern from the radiation emitted from the radiation source, and
   at least two cameras for imaging the pattern projected on the object, the cameras being arranged for having an overlapping field of view on the object,
   wherein:
   the pattern is a non-periodic dot pattern generated by a two-dimensional array of microlenses arranged on a substrate in a non-periodic manner, and
   the array of microlenses is the last beam shaping optical element before the object.

2. The intraoral scanner of claim 1, wherein the rays of the beam arriving at the microlenses are not collimated.

3. The intraoral scanner of claim 1, wherein the beam comprises subbeams formed by the microlenses and wherein the subbeams converge on the object side of the array of microlenses.

4. The intraoral scanner of claim 1, wherein the working distance, at which the size of the dots is at a minimum, is greater than the focal length of the microlenses, the working distance and the focal length each being measured in radiation direction from the base of the microlenses on the surface of the substrate.

5. The intraoral scanner of claim 1, wherein the subbeams are deflected in a lateral direction by at least one mirror positioned in front of and/or behind the array of microlenses in the direction of the radiation.

6. The intraoral scanner of claim 5, wherein the mirror deflects incoming light towards the cameras.

7. The intraoral scanner of claim 1, wherein the microlenses are arranged in a honeycomb structure, the center of each microlens being shifted off-center from the center of the corresponding honeycomb cell by a randomly selected distance and direction.

8. The intraoral scanner of claim 1, wherein the radiation source is a laser diode and wherein the divergence of the beam emerging from the laser diode is homogenized by an optical element located between the laser diode and the array of microlenses.

9. The intraoral scanner of claim 1, wherein the cameras are oriented in the same direction.

10. The intraoral scanner of claim 1, wherein the center of the array of microlenses is located at a distance from the baseline between the cameras.

11. The intraoral scanner of claim 10, wherein the array of microlenses is tilted by an angle $\alpha$ towards an axis at right angle to a beam axis of the beam.

12. The intraoral scanner of claim 11, wherein the angle $\alpha$ is generally more than half of an angle $\beta$ between the beam axis and an axis of a field of view of the cameras if viewed along a frontside of the substrate.

13. An intraoral scanning system for generating a three-dimensional model of a dentition based on active stereo vision comprising:

an intraoral scanner having a projector for projecting a structured pattern onto the dentition to be three dimensionally modelled, the projector having a radiation source emitting a beam and optics for generating the structured pattern from the radiation emitted from the radiation source, and at least two cameras for imaging the pattern projected on the object, the cameras being arranged for having an overlapping field of view on the object, wherein the pattern is a non-periodic dot pattern generated by a two-dimensional array of microlenses arranged on a substrate in a non-periodic manner, and the array of microlenses is the last beam shaping optical element before the object, wherein each camera generates a series of images of the patterns projected onto the dentition, and a data processing unit connected to the intraoral scanner for generating the three-dimensional model of the dentition based on disparity maps formed by means of a synchronized series of images generated by each camera.

14. The intraoral scanning system of claim 13, wherein the data processing unit is arranged for performing the following acts:

capturing a series of synchronized images by means of the at least two cameras;

generating the disparity maps based on pairs of synchronized images, wherein each image is taken from a different camera;

generating depth maps based on the disparity maps;

registration of the depth maps;

forming a mesh of points defining the surface of the imaged dentition.

15. A method for generating a three-dimensional model of a dentition based on active stereo vision, comprising:

retrieving a series of images of the dentition from an intraoral scanner having a projector for projecting a structured pattern onto the dentition to be three dimensionally modelled, the projector having a radiation source emitting a beam and optics for generating the structured pattern from the radiation emitted from the radiation source, and at least two cameras for imaging the pattern projected on the object, the cameras being arranged for having an overlapping field of view on the object, wherein the pattern is a non-periodic dot pattern generated by a two-dimensional array of microlenses arranged on a substrate in a non-periodic manner, and the array of microlenses is the last beam shaping optical element before the object;

using a data processing unit connected to the intraoral scanner for generating the three-dimensional model of the dentition based on disparity maps formed by the series of images generated by each camera.

16. A non-transitory computer readable medium encoded with computer executable instructions that when executed by the computer generate a three-dimensional model of a dentition by the following steps:

retrieving a series of images of the dentition from an intraoral scanner having a projector for projecting a structured pattern onto the dentition, the projector having a radiation source emitting a beam and optics for generating the structured pattern from the beam, and at least two cameras for imaging the structured pattern projected onto the dentition, the at least two cameras being arranged for having an overlapping field of view on the dentition, wherein the structured pattern is a non-periodic dot pattern generated by a two-dimensional array of microlenses arranged on a substrate in a non-periodic manner, and the array of microlenses is the last beam shaping optical element before the dentition;

generating the three-dimensional model of the dentition based on disparity maps formed by the series of images generated by each camera.

* * * * *